United States Patent [19]

Cathignol et al.

[11] Patent Number: 4,868,791

[45] Date of Patent: Sep. 19, 1989

[54] METHOD AND APPARATUS FOR DETECTING AND CORRECTING THE POSITIONS OF ELECTRODES, IN PARTICULAR IN SHOCK WAVE GENERATOR APPARATUS USING A FEELER FINGER, E.G. THE ROD OF AN ACTUATOR, MOVABLE TO THE FOCUS

[76] Inventors: Dominique Cathignol, 14, rue du Fort, 69740 Genas; Bernard Lacruche, 21, Rue de la Part-Dieu, 69003 Lyon, both of France

[21] Appl. No.: 163,988

[22] Filed: Mar. 4, 1988

[30] Foreign Application Priority Data

Mar. 9, 1987 [FR] France ................................ 87 03184

[51] Int. Cl.[4] .......................... G01V 1/00; A61B 17/22

[52] U.S. Cl. .................................. 367/13; 128/24 A; 367/147

[58] Field of Search ............... 181/113, 116, 117, 118, 181/108; 367/13, 147; 73/866.5, 432.1, 1 R; 128/328, 24 A; 324/347, 359

[56] References Cited

U.S. PATENT DOCUMENTS

| | | | |
|---|---|---|---|
| 2,559,227 | 7/1951 | Rieber | 367/147 |
| 3,942,531 | 3/1976 | Hoff et al. | 128/328 |
| 4,608,983 | 9/1986 | Muller et al. | 128/328 |
| 4,730,614 | 3/1988 | Lachruche et al. | 128/328 |
| 4,734,894 | 3/1988 | Cannelli et al. | 367/147 |

FOREIGN PATENT DOCUMENTS 307507 12/1916 Fed. Rep. of Germany .

*Primary Examiner*—Brian S. Steinberger

*Attorney, Agent, or Firm*—Schechter Brucker & Pavane

[57] ABSTRACT

The invention relates to a method and to apparatus for detecting and correcting the positions of electrodes. The device comprises means for advancing the electrodes to cause them to advance and retract, preferably in an individual and independent manner, together with detector means (10) capable of being disposed at and of being retracted from the focus (F) at which an electric arc or discharge is to be provided between the electrodes (2, 4) and said detector means being suitable for detecting the presence of an electrode at said focus. Position correction then consists in successively bringing each electrode to the focus (F) into contact with said detector means which are advantageously constituted by a rod (12) of an actuator (14), prior to retracting each electrode through a predetermined distance d. The invention makes it possible to detect and correct the positions of electrodes at will, in an entirely simple manner capable of being automated.

19 Claims, 2 Drawing Sheets

METHOD AND APPARATUS FOR DETECTING AND CORRECTING THE POSITIONS OF ELECTRODES, IN PARTICULAR IN SHOCK WAVE GENERATOR APPARATUS USING A FEELER FINGER, E.G. THE ROD OF AN ACTUATOR, MOVABLE TO THE FOCUS

The present invention relates essentially to a method and to apparatus for detecting and correcting the positions of electrodes, in particular in a shock wave generator apparatus using a feeler finger, e.g. The rod of an actuator, movable to the focus.

BACKGROUND OF THE INVENTION

U.S. Pat. No. 2,559,227 (Rieber) describes a high frequency shock wave generator apparatus comprising a reflector 80 in the form of a truncated ellipsoid suitable for reflecting shock waves, said reflector comprising a cavity 80A constituting a reflection chamber for said shock waves and having the same truncated ellipsoidal shape, with one of the two focuses of the ellipsoid being disposed inside the chamber at its nontruncated end, and with said chamber being filled with a shock wave transmitting liquid 83, e.g. an oil. This apparatus also includes a shock wave generator device which is generally constituted by two electrodes 12 and 13 and which is at least partially disposed inside the chamber 80A, having the two electrodes disposed to generate an electric arc or discharge at the focus which is situated inside the chamber away from the truncated portion of the ellipsoid, and with means 10 and 11 being provided to selectively deliver an instantaneous electrical voltage to the electrodes 12 and 13, thereby giving rise to an electric arc or discharge between the electrodes and thus generating shock waves in the liquid contained in the chamber (see FIG. 3 and column 7, line 51 to column 9, line 30).

The electrodes 12 and 13 are made of a highly conductive material such as copper or brass and they are mounted on an insulator 26 which is pivotally supported by means of a device 11a, 11b for adjusting the spacing therebetween (see column 4 lines 42 to 53 and column 8, lines 41 to 47).

Patent document U.S. Pat. No. 3,942,531 also describes a similar apparatus in which the liquid is constituted by water (see page 3, lines 23 to 24).

When employing a Rieber apparatus or a similar apparatus, it has been observed that a discharge at the electrodes is accompanied by metal being torn away therefrom, thus wearing the electrodes in a manner which is a function of the discharge current that sets up a plasma between the electrodes and generates a sudden pressure wave. The electrodes wear relatively quickly, for example using electrodes having a diameter of 2 mm and made of Z 80 steel, the speed of wear is 1 mm per 800 discharges, and this constitutes a major drawback which greatly increases the cost of using the apparatus.

Proposals have already been made in U.S. Pat. No. 4,608,983 to provide an electrode-advancing device 36, 38 (FIG. 3) including a control member 48 which controls simultaneous advance or retraction movement of the electrodes by being rotated in one direction or the other (see page 9, line 11 to page 10, line 11).

Implementing the structure for supporting and advancing the electrodes is relatively complicated and high in price.

Proposals have also been made in U.S. Pat. No. 4,730,614 concerning devices for advancing electrodes which are much simpler to implement, and which provide greater accuracy in advancing the electrodes.

However, none of these prior apparatuses makes it possible to detect the amount of electrode wear with a high degree of accuracy.

Further, none of these prior apparatuses makes it possible to detect and correct the position of the electrodes at any moment.

Said method and apparatus recently proposed by the Applicants provide entire satisfaction.

However, for industrial applications, it is necessary to simplify the method of detecting and correcting the position of the electrodes, and to provide a device which is easy to implement, which is cheap, and which is highly reliable.

Further, when the prior device is permanently mounted on the ellipsoidal reflector, as is desirable, the vibrations emitted during discharges may damage the device. Also, the differences in light intensity between two different bulbs require the system to be recalibrated. Shock waves which are repeated thousands of times may damage the protective glass, and deposits may occur on the glass, thereby changing the setting of the detector device which is generally of the CCD type.

Preferred implementations of the present invention therefore solve a new technical problem of enabling the position of each of the electrodes to be detected with high accuracy or precision in order to enable the positions of the electrodes to be corrected at any moment with high accuracy or precision; this solution should be of a particularly simple design, highly practical to implement at low cost, and very reliable for use in an industrial application.

Preferred implementations of the present invention also seek to provide a method and apparatus for detecting and correcting the position of electrodes applicable to all types of electrode-using apparatuses, but preferably particularly suitable for use in shock wave generator apparatuses, and also preferably in such apparatuses which include a shock wave generator device including a truncated ellipsoidal reflector.

These technical problems are solved for the first time by the present invention in a satisfactory manner.

SUMMARY OF THE INVENTION

Thus, in a first aspect, the invention provides a method of detecting and correcting the positions of electrodes, in particular the electrodes used in shock wave generator apparatuses, said electrodes needing to be disposed at a predetermined distance symmetrically about a specified point in three dimensions at which an electric arc or discharge is to be generated between the electrodes, said point being referred to as the focus, the method being characterized in that it comprises the following steps:

providing detector means capable of detecting the presence of an electrode and disposing said detector means at a predetermined point in three dimensions, referred to as the "detection" point, said detection point being situated at one of the foci and on the path of electrode displacement, said detector means being suitable for detecting the presence of an electrode at said detection point;

advancing one of the electrodes until it comes into contact with said detector means disposed at said detection point;

detecting the presence of the electrode at said detection point;

retracting the electrode so as to position it at said predetermined distance therefrom;

following the same procedure for the, or each, other electrode; and retracting said detector means from said detection point;

thereby enabling the position of the electrodes to be corrected at will regardless of whether the electrodes are new or worn after being used for a certain number of discharges.

Preferably, the detection point coincides with the focus.

In a particular implementation of the method, said detector means comprises a feeler finger which is moved to the detection point so as to constitute an obstacle to advancing each electrode.

In a particular preferred implementation of the method, said detector means comprises a feeler finger which is moved to the detection point so as to constitute an obstacle to advancing each electrode.

In a particular preferred implementation, said feeler finger is constituted by the rod of an actuator whose displacement axis lies in a plane passing through the detection point, perpendicularly to the electrode advance axis, and advantageously coinciding with the axis of the ellipsoidal reflector.

In a variant implementation of the invention, said detector means may be constituted by a light beam or by a beam of electromagnetic waves.

In accordance with a particularly advantageous feature of the invention, the presence of an electrode at the detection point is detected by detecting the variation in the resistance between the detector means and the electrode, which electrode is at least momentarily grounded.

According to a second aspect, the present invention also provides a device for detecting and correcting the positions of electrodes, in particular electrodes used in shock wave generator apparatuses, said electrodes needing to be disposed at a predetermined distance symmetrically about a specified point in three dimensions at which an electrical arc or discharge is to be generated between said electrodes, electrode advance means being provided for advancing and retracting the electrodes, preferably individually and independently, wherein the device comprises detector means movably mounted in said device to be disposed at and retracted from a predetermined point in space, referred to as the detection point and situated at one of the foci and on the path over which the electrodes move, said detector means detecting the presence of an electrode at said detection point.

In a preferred embodiment, said detector means comprises a feeler finger capable of being moved to the detection point in order to constitute an obstacle to advancing the electrode.

In a particular embodiment, said feeler finger is constituted by the rod of an actuator whose displacement axis lies in a plane passing through the detection point, perpendicularly to the advance axis of the electrodes.

In accordance with the a particular feature, the detector means comprises a device for measuring the electrical resistance between the feeler finger and the electrode, and means for indicating a variation in said resistance.

According to another particular feature, said device comprises means for momentarily grounding the positive electrode.

According to another feature of the invention, said actuator rod is in electrical contact with the body of the actuator, thereby facilitating the measurement of the electrical resistance between the feeler finger and the electrode.

In accordance with another advantageous feature it is possible to provide the device in accordance with the invention with means for detecting mechanical contact between the electrodes.

It is also possible, in accordance with another particular feature, to provide for the device in accordance with the invention to optionally include a contact for indicating that the actuator piston is in a retracted position.

In accordance with another particularly advantageous feature, it is possible for the means that momentarily ground the positive electrode to include a switch in the form of a double-acting contact.

For safety reasons, the switch connected to the positive electrode may also include a very fine wire or fuse which is destroyed in the event of a high current being passed.

It can thus be understood that the present invention makes it possible to detect the position of each of the electrodes with a high degree of accuracy and to correct said position very accurately by correcting the distance between the electrode and the focus at which the electric arc or discharge is to be provided so as to ensure that said position is substantially equal to a predetermined reference value.

This correction may advantageously be provided in an extremely simple manner by issuing "advance" instructions to devices for advancing electrodes as described in the commonly assigned U.S. Pat. No. 4,730,614.

BRIEF DESCRIPTION OF THE DRAWINGS

The presently preferred implementation of the invention is described by way of example with reference to the accompanying drawings, in which.

DESCRIPTION OF THE PREFERRED IMPLEMENTATION

Figure 1:
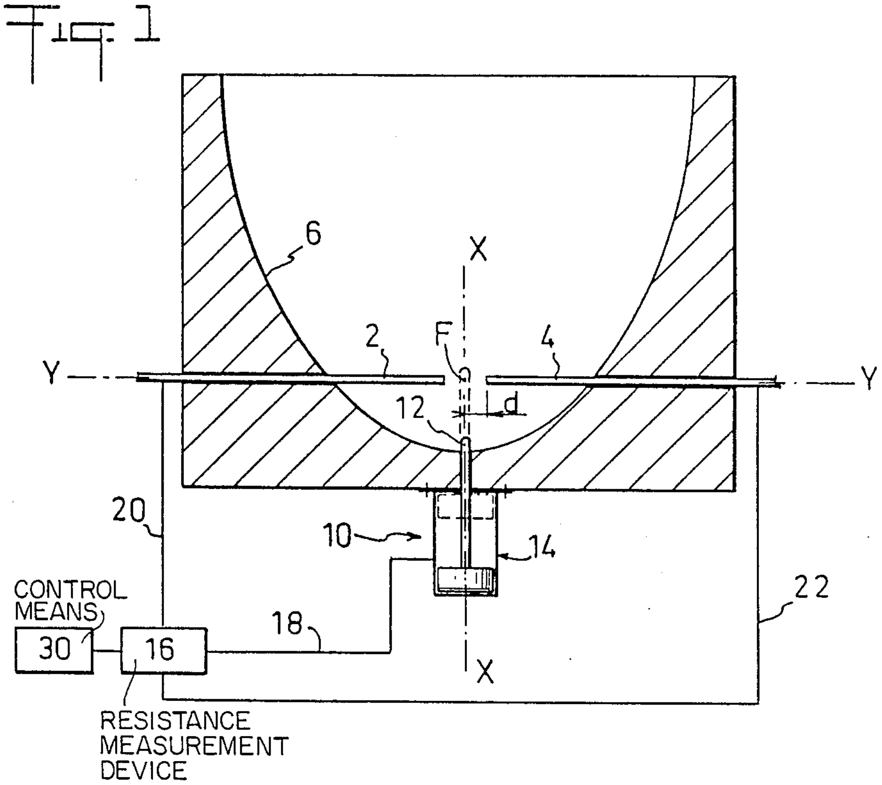
FIG. 1 shows the presently preferred embodiment of a device for detecting and correcting the position of electrodes in accordance with the invention and used, in the example shown, in a shock wave generator apparatus including a truncated ellipsoidal reflector of the type described in Rieber's U.S. patent, with the figure being a longitudinal section passing both through the focus and through the plane of the electrodes.
Figure 2A:
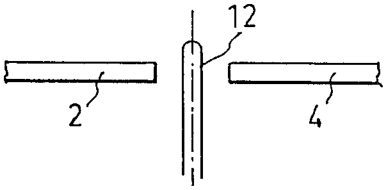
FIGS. 2*a* and 2*b* are detail views on a larger scale showing the detector means which is preferably at the focus in this case, with the electrodes being shown in their initial positions (FIG. 2*a*), in a contact position (FIG. 2*b*), and in a retracted position shown in dashed lines (FIG. 2*b*) where the electrode is retracted through a predetermined distance.
Figure 2B:
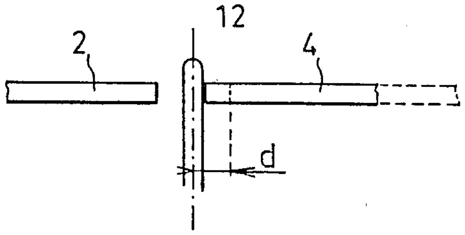
Figure 3:
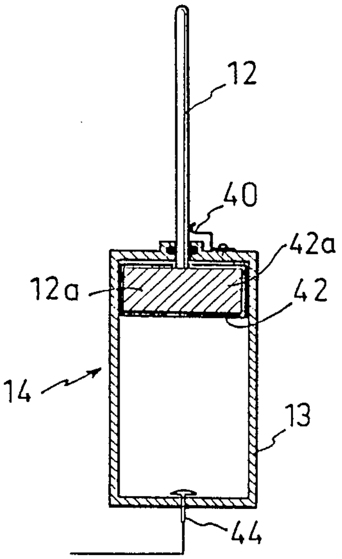
FIG. 3 is a detailed view on a larger scale through the body of the actuator which constitutes a particular detector means.

With reference to the figures, and in particular with reference to FIGS. 1 to 3, the presently preferred embodiment of a device for detecting and correcting the positions of electrodes 2 and 4 is shown. In the example shown, these electrodes are used in shock wave generator apparatus including a truncated ellipsoidal reflector 6 of the type describe in U.S. Pat. No. 2 559 227 (Rieber).

In order to operate properly, the electrodes 2 and 4 must be disposed at a predetermined distance d symmetrically about a three-dimensionally specified point F where the electric arc or discharge is intended to be generated between the electrodes, with said point being normally referred to as the focus.

According to the present invention, the device for detecting and correcting positions of the electrodes 2 and 4 is characterized in that it comprises detector means given a general reference numeral 10 displaceably mounted in the device to be disposed at a predetermined point in three dimensions, referred to as the "detection point", said detection point being situated either at the focus or else on the path followed by the electrodes when being advanced thereto or retracted therefrom, and in detecting the presence of an electrode at said point. Preferably, as shown, the detection point coincides with the focus (F).

In a particular embodiment, this detector means 10 comprises a feeler finger 12 suitable for being moved to the focus F in order to constitute an obstacle to the advance of electrode 2 or 4, as is clearly shown in FIG. 2.

In the presently preferred embodiment, this feeler finger 12 is constituted by the rod of an actuator 14 whose displacement axis X—X lies in a plane passing through the focus and extending perpendicularly to the electrode advance axis Y—Y.

In a particular embodiment, said detector means 10 comprises a device 16 for measuring the electrical resistance between the feeler finger 12 and the electrode (2 or 4) via suitable electrical conductors 18, 20, and 22. This measurement device 16 may also incorporate a component for indicating a change in resistance and may also transmit data to control means 30, which control means may include a computer suitable for transmitting instructions to the means for advancing the electrodes 2 and 4, which means are provided to advance or retract the electrodes, preferably individually and independently of each other, said means for advancing the electrodes being preferably as described in commonly assigned U.S. Pat. No. 4,730,614.

It will thus be understood that the detector means 10 may also include means for detecting mechanical or physical contact between the electrodes. In this case, given that each of the electrodes 2 and 4 is connected to the measurement device 16 via a conductor 20 or 22, it suffices to measure the electrical resistance between the electrodes via said conductors 20 and 22 in order to detect contact between the electrodes, as explained below when explaining the operation of said device in accordance with the invention.

Figure 4:
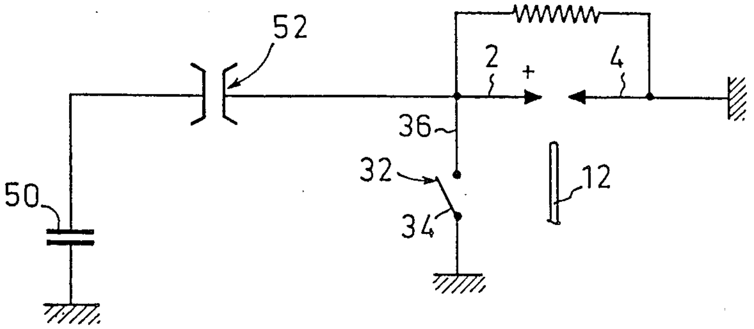
FIG. 4 is an electric circuit diagram for detecting the position of the electrodes by measuring the electrical resistance between the detector means and the electrodes.

Advantageously, means 32 are provided in accordance with the invention for momentarily grounding the positive electrode, for example the electrode 2, in this case. It is normally not necessary to provide such means for the negative electrode since the negative electrode is permanently grounded. Preferably, the means 32 for momentarily grounding the positive electrode is constituted by a switch 34 which is advantageously a double-action switch so as to have an out-of circuit position and a ground circuit closure position. The out-of-circuit position is shown in FIG. 4.

For safety reasons, the means 32 for momentarily grounding the positive electrode may be provided via a contact that operates as a fuse and is suitable for being destroyed in the event of a high-voltage current being passed. This can be achieved by using a very fine wire 36 between the switch 34 and the positive electrode, in this case electrode 2. It would naturally be possible simply to install a fuse on said conductor 36.

Normally, an actuator rod is insulated from the body of the actuator.

As a result, in order to provide electrical contact between the rod 12 and the body 13 of actuator 14, an electrical contact 40 may be provided, for example fixed on the body 13 of the actuator 14 and slidably bearing against the rod 12. This contact may be a simple metal blade.

A variant method of putting the actuator rod 12 into electrical contact with the body 13 of the actuator 14 (with each of them naturally being electrically conductive) is to provide a sealing ring of conductive silicone 42 around the piston 42*a* which is fixed to the rod 12.

It is also possible to provide a position contact 44 for indicating that the piston 12*a* of the actuator 14 is in the retracted position. Said contact 44 is thus at the rear or base of the body 13 of the actuator 14, as shown in FIG. 3. It can be understood from the above that the device in accordance with the invention enables the method of detecting and correcting the positions of the electrodes as described above to be performed.

Initially, the rod 12 of the actuator 14 is placed at the focus F by acting on the actuator 14 which may be a pneumatic actuator, for example. Said rod 12 constitutes an integral portion of the detector means 10, and normally the electrodes 2 and 4 are situated on either side of the rod 12, as shown in FIG. 2.

Thereafter, one of the electrodes, in this case electrode 4, is advanced until it comes into contact with the rod 12 disposed at the focus F and constituting an integral portion of the detector means 10.

At which point the presence of the electrode (in this case electrode 4) at the focus F is detected by virtue of it coming into contact with the rod 12. This is done by measuring the resistance between the rod 12 and the electrode (in this case electrode 4), i.e. by measuring the resistance at measurement device 16 of the circuit comprising: electrical conductor 18; actuator body 13; actuator rod 12; electrode 4; and conductor 22.

When the electrode (in this case electrode 4) comes into contact with the rod 12, the resistance falls off suddenly.

Having detected this sudden drop in resistance, the electrode (in this case electrode 4) is retracted through a predetermined distance d in order to ensure that the electrode 4 is in the proper position relative to the focus F.

The same procedure is followed with each, other electrode.

In this case, since the electrode 2 is the positive electrode, in order to proceed with the above operations, the positive electrode is initially grounded by closing switch 34. The resistance in the following circuit is then detected: conductor 20; electrode 2; rod 12; actuator body 13; and conductor 18. The drop in resistance which occurs on contact between the electrode 2 and the rod 12 is then detected in the same manner, prior to retracting said electrode 2 through the same predetermined distance d. Devices 16 for measuring resistance are well known to the person skilled in the art and need no further explanation herein. The device may be a simple ohmmeter.

Naturally, after the measurement has been performed, the switch 34 is returned to the open, out-of-circuit position as shown in FIG. 4.

It will be understood that the method and the device in accordance with the invention can be used to accurately detect and correct the position of the electrodes.

It will be observed that said method and apparatus are well adapted to being fully automated since when there is no contact between the electrode being monitored and the rod 12 via the detector 10, a numerical value 0 may be attributed to the situation, and when contact occurs and the resistance falls suddenly, numerical value 1 may be attributed to the situation, thereby enabling the data to be processed by computer means.

Further, assuming that the actuator 14 breaks down, and rod 12 is not advanced while an electrode is being advanced, the electrode will end up coming into contact with the other electrode. This defect may be detected by detecting contact between the two electrodes by means of the measurement device 16 detecting the resistance via conductors 20 and 22 connected to electrodes 2 and 4 respectively.

If the actuator does not return to its initial retracted position, this fault can be detected by the absence of contact between the contact 44 and the piston 12*a* of the rod 12. It will be understood that these safety measures are essential and must be reliable since it is essential for the rod 12 to be retracted from the focus F in order to generate shock waves properly at the focus F.

Further, it is also essential for the means for momentarily grounding the positive electrode (in this case electrode 2) to be in the open or out-of-circuit position so as to avoid short circuiting the electric current fed to the positive electrode 2 from capacitor 50 which advantageously includes spark gap discharge means 52 well known to the person skilled in the art. For safety reasons, in this extreme case, either the conductor wire 36 between the positive electrode 2 and the grounding means 32 is very fine and suitable for being destroyed if it should pass a high-voltage current, or else a fuse is provided therein for performing the same role.

Finally, in the event of the electrodes being initially excessively off-center and the rod 12 being incapable of advancing as far as the focus F because there is an electrode at the focus, contact is nevertheless detected and it is necessary to retract the electrode. Thereafter the situation returns to the conventional case shown in FIG. 2.

It can thus be understood that the invention includes any means constituting technical equivalence to the means described and shown, and also to various combinations thereof.

We claim:

1. In a method of detecting and correcting the positions of electrodes to a predetermined distance d symmetrically about a specified point in three dimensions at which an electric arc is to be generated between the electrodes, said point being referred to as the focus, said method comprising the following steps:

(a) providing detector means capable of detecting the presence of an electrode and disposing said detector means at a predetermined point in three dimensions, referred to as the "detection" point, said detection point being situated on the path of electrode displacement, said detector means being suitable for detecting the presence of an electrode at said detection point;

(b) advancing one of the electrodes until said one electrode comes into contact with said detector means disposed at said detection point;

(c) detecting the presence of the electrode at said detection point;

(d) retracting said one electrode so as to position it at said predetermined distance d therefrom;

(e) repeating steps (b)-(d) for each other electrode; and (f) retracting said detector means from said detection point; thereby enabling the position of the electrodes to be corrected regardless of the number of discharges for which the electrodes have been used.

2. The method of claim 1, wherein the detector means includes a feeler finger which is moved to the detection point in order to constitute an obstacle to advancing each of the electrodes.

3. The method of claim 2, wherein the feeler finger is constituted by the rod of an actuator whose displacement axis lies in a plane passing through the detection point, perpendicularly to the advance axis of the electrodes.

4. The method according to claim 1, wherein said detection point is said focus.

5. The method of claim 1, wherein the presence of the electrode at the detection point is detected by detecting a variation in the resistance between the detector means and the electrode, which electrode is grounded, at least momentarily.

6. The method of claim 1, wherein the electrodes are mounted in a shock wave generator apparatus.

7. A device for detecting and correcting the positions of electrodes to a predetermined distance d symmetrically about a specified point in three dimensions at which an electrical arc or discharge is to be generated between said electrodes, said point being referred to as the focus, electrode advance means being provided for advancing and retracting each electrode, wherein the device comprises detector means movably mounted in said device to be disposed at and retracted from a predetermined point in space, referred to as the detection point and situated on the path over which the electrodes move, said detector means detecting the presence of an electrode at said detection point.

8. The device of claim 7, wherein the above-mentioned detector means comprises a feeler finger capable of being moved to the detection point in order to constitute an obstacle to the advance of the electrode.

9. The device of claim 7, wherein the feeler finger is constituted by the rod of an actuator whose displacement axis lies in a plane passing through the detection point perpendicularly to the electrode advance axis.

10. The device of claim 9, wherein said actuator includes a piston; and further comprising a position contact for detecting the piston in the retracted position.

11. The device of claim 9, wherein the rod of the actuator is in electrical contact with the body of the actuator.

12. The device of claim 7, wherein the detector means comprises a feeler finger and a device for measuring electrical resistance between the feeler finger and the electrode; and means for indicating variation in said resistance.

13. The device of claim 7, wherein one of said electrodes comprises the positive electrode, and further comprising means for grounding the positive electrode.

14. The device of claim 13, wherein the means for grounding the positive electrode is a switch.

15. The device of claim 14, wherein the switch is connected to the electrode by means of a fuse for protecting the electrode.

16. The device of claim 7, comprising means for detecting mechanical contact between the electrodes.

17. The device of any one of claims 7 to 11, wherein the electrodes are mounted in a shock wave generator apparatus.

18. A shock wave generator apparatus comprising a device for detecting and correcting the positions of electrodes as defined in any one of claims 7 to 11.

19. The device according to claim 7, wherein said detection point is said focus.

* * * * *